US012222285B2

(12) United States Patent
Gollihar

(10) Patent No.: US 12,222,285 B2
(45) Date of Patent: Feb. 11, 2025

(54) HANDHELD OBJECT ASSESSMENT SYSTEM AND METHOD

(71) Applicant: DISH Wireless L.L.C., Englewood, CO (US)

(72) Inventor: William Allen Gollihar, Castle Rock, CO (US)

(73) Assignee: DISH Wireless L.L.C., Englewood, CO (US)

( * ) Notice: Subject to any disclaimer, the term of this patent is extended or adjusted under 35 U.S.C. 154(b) by 250 days.

(21) Appl. No.: 18/164,489

(22) Filed: Feb. 3, 2023

(65) Prior Publication Data

US 2024/0264080 A1    Aug. 8, 2024

(51) Int. Cl.
| | |
|---|---|
| *G01N 21/39* | (2006.01) |
| *G01N 21/31* | (2006.01) |
| *G01N 21/359* | (2014.01) |
| *G01N 33/02* | (2006.01) |

(52) U.S. Cl.
CPC ......... *G01N 21/39* (2013.01); *G01N 21/3103* (2013.01); *G01N 21/359* (2013.01); *G01N 33/025* (2013.01); *G01N 2201/06113* (2013.01)

(58) Field of Classification Search
CPC .. G01N 21/39; G01N 21/3103; G01N 21/359; G01N 33/025

USPC ......................................... 356/300
See application file for complete search history.

(56) References Cited

U.S. PATENT DOCUMENTS

| | | | | |
|---|---|---|---|---|
| 2013/0265566 A1* | 10/2013 | Smith | ................... | G01N 21/359 |
| | | | | 356/402 |
| 2015/0144791 A1* | 5/2015 | Simpkin | .............. | G01N 21/359 |
| | | | | 356/320 |

\* cited by examiner

*Primary Examiner* — Md M Rahman
(74) *Attorney, Agent, or Firm* — Seed IP Law Group LLP

(57) ABSTRACT

A handheld object assessment system includes a laser array, a detector array configured to detect reflection of laser emissions, and a control system having a memory and a processor. The control system to: initiate laser emissions at multiple different wavelengths directed towards an object being assessed, detect an amount of the laser emissions at the multiple different wavelengths that were reflected from the object being assessed, determine an amount of laser emissions that were absorbed into the object being assessed at the multiple different wavelengths, determine one or more parameters regarding the object being assessed by comparing the amount of laser emissions that were absorbed and the amount of laser emissions that were reflected, and notify a user of the handheld object assessment system of the one or more parameters of the object being assessed that were determined.

19 Claims, 7 Drawing Sheets

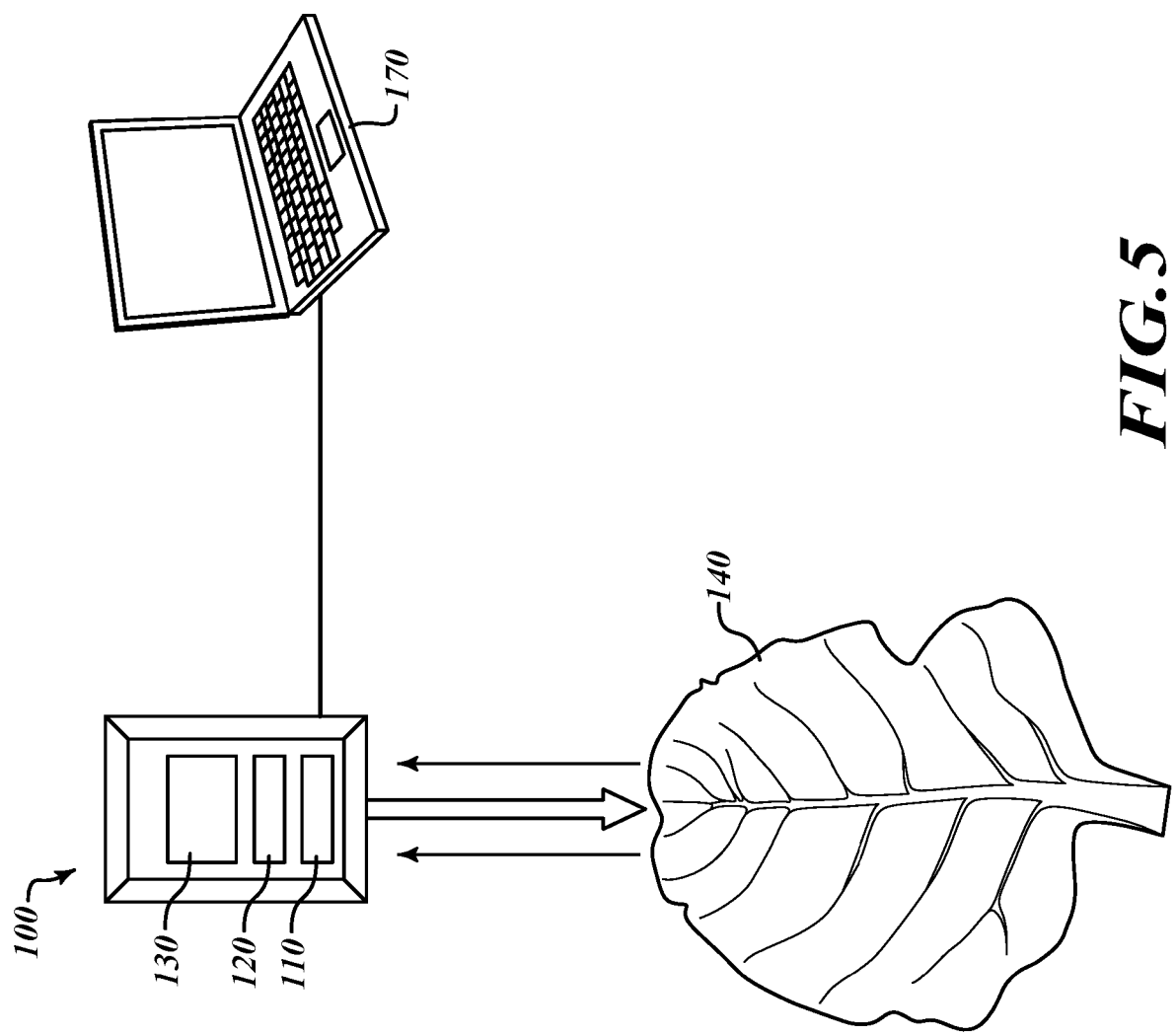

HANDHELD OBJECT ASSESSMENT SYSTEM AND METHOD

BACKGROUND

In some industrial and agricultural operations as well as other operations, there are times when operators or other users would like to perform assessments or obtain analysis of various types of objects. Some such assessments or analysis may be for determining a composition of an object. Other assessments or analysis may be for determining experimental data about an object.

Many current methods for assessments or analysis result in the partial or total destruction of the object being tested, which is often undesirable. Additionally, many such methods for assessments or analysis require large amounts of expensive equipment and time consuming testing procedures. There is a continuing need in the art regarding assessments or analysis methods that do not have these types of technological shortcomings.

BRIEF SUMMARY

The present disclosure relates generally to a system and method for assessing information about objects using a handheld device.

There are several technological improvements provided by the disclosed system for assessing an object, including the prompt and efficient ability to determine whether or not a chemical agent, biological agent, or allergen is present or absent in association with the object being assessed. Moreover, the system for assessing an object may perform a chemical analysis of the object being assessed and provide information regarding one or more parameters of the object being assessed based on the chemical analysis.

In one or more embodiments, a system for assessing an object is disclosed that includes a handheld object assessment system having a laser array configured to emit lasers with multiple different wavelengths, a detector array configured to detect reflection of laser emissions at the multiple different wavelengths, and a control system having a memory that stores computer instructions and a processor that executes the computer instructions. The processor-executed computer instructions cause the control system to: initiate, using the laser array of the handheld object assessment system, laser emissions at the multiple different wavelengths directed towards an object being assessed; detect, using the detector array of the handheld object assessment system, an amount of the laser emissions at the multiple different wavelengths that were reflected from the object being assessed; determine, using the processor of the handheld object assessment system, an amount of laser emissions that were absorbed into the object being assessed at the multiple different wavelengths, based at least in part on the detected reflections of the laser emissions from the object being assessed at the multiple different wavelengths and the initiated laser emissions directed towards an object being assessed at the multiple different wavelengths; determine, using a processor of the handheld object assessment system, one or more parameters of the object being assessed by comparing the amount of laser emissions that were absorbed into the object being assessed at the multiple different wavelengths and the amount of laser emissions that were reflected from the object being assessed at the multiple different wavelengths; and notify a user of the handheld object assessment system of the one or more parameters of the object being assessed that were determined.

In some embodiments, the laser array of the handheld object assessment system is configured to emit lasers at three distinct wavelengths towards the object being assessed. In another aspect of some embodiments, the three distinct wavelengths are 850 nanometers, 1380 nanometers, and 1850 nanometers. In still another aspect of some embodiments, the three distinct wavelengths are in a range of 750-950 nanometers, 1280-1480 nanometers, and 1750-1950 nanometers. In yet another aspect of some embodiments, a larger percentage of absorbed laser emissions with respect to the reflected laser emissions indicates a first parameter of the one or more parameters of the object being assessed, and a smaller percentage of absorbed laser emissions with respect to the reflected laser emissions indicates a second parameter of the one or more parameters of the object being assessed.

In one or more embodiments, the object being assessed is a fruit or vegetable, and the first parameter of the one or more parameters is a first state of ripeness and the second parameter of the one or more parameters is a second state of ripeness. In another aspect of some embodiments, the object being assessed potentially includes a chemical agent, biological agent, or allergen, wherein the first parameter of the one or more parameters of the object being assessed is a presence of the chemical agent, biological agent, or allergen, and wherein the second parameter of the one or more parameters of the object being assessed is an absence of the chemical agent, biological agent, or allergen. In still another aspect of some embodiments, the laser array of the handheld object assessment system includes a plurality of lasers configured to emit laser emissions that are fixed at specific wavelengths. In yet another aspect of some embodiments, the laser array of the handheld object assessment system emit laser emissions that are tunable to specific wavelengths. Further, in another aspect of some embodiments, the handheld object assessment system is incorporated into a smartphone or a smartphone case.

In one or more embodiments, a method for assessing an object is disclosed that includes: providing a handheld object assessment system that includes a laser array configured to emit lasers with multiple different wavelengths and a detector array configured to detect reflection of laser emissions at the multiple different wavelengths; initiating, using the laser array of the handheld object assessment system, laser emissions at the multiple different wavelengths directed towards an object being assessed, wherein in response to the laser emissions reaching the object being assessed, some of the laser emissions are absorbed into the object being assessed at the multiple different wavelengths and some of the laser emissions are reflected from the object being assessed at the multiple different wavelengths; detecting, using the detector array of the handheld object assessment system, an amount of the laser emissions at the multiple different wavelengths that were reflected from the object being assessed; determining, from the detected reflections of the laser emissions from the object being assessed at the multiple different wavelengths and the initiated laser emissions at the multiple different wavelengths directed towards an object being assessed, an amount of laser emissions that were absorbed into the object being assessed at the multiple different wavelengths; determining, using a processor of the handheld object assessment system, one or more parameters of the object being assessed by comparing the amount of laser emissions that were absorbed into the object being assessed at the multiple different wavelengths and the amount of laser emissions that were reflected from the object being assessed at the multiple different wavelengths; and notifying a user of the handheld object assessment system of the one or more parameters of the object being assessed that were determined.

In some embodiments, the method further includes emitting lasers from the laser array at three distinct wavelengths towards the object being assessed. In another aspect of some embodiments, the three distinct wavelengths of lasers emitted from the laser array are 850 nanometers, 1380 nanometers, and 1850 nanometers. In still another aspect of some embodiments, the three distinct wavelengths of lasers emitted from the laser array are in a range of 750-950 nanometers, 1280-1480 nanometers, and 1750-1950 nanometers. In yet another aspect of some embodiments, a larger percentage of absorbed laser emissions with respect to the reflected laser emissions indicates a first parameter of the one or more parameters of the object being assessed, and a smaller percentage of absorbed laser emissions with respect to the reflected laser emissions indicates a second parameter of the one or more parameters of the object being assessed.

In one or more embodiments, the object being assessed is a fruit or vegetable, and the first parameter of the one or more parameters is a first state of ripeness and the second parameter of the one or more parameters is a second state of ripeness. In another aspect of some embodiments, the object being assessed potentially includes a detectable chemical agent, biological agent, or allergen, wherein the first parameter of the one or more parameters of the object being assessed is a presence of the chemical agent, biological agent, or allergen, and wherein the second parameter of the one or more parameters of the object being assessed is an absence of the chemical agent, biological agent, or allergen. In still another aspect of some embodiments, the method further includes constructing the laser array of the handheld object assessment system to include a plurality of lasers configured to emit laser emissions that are fixed at specific wavelengths. In yet another aspect of some embodiments, the method further includes constructing the laser array of the handheld object assessment system to produce laser emissions that are tunable to specific wavelengths. Further, in another aspect of some embodiments, the method further includes incorporating the handheld object assessment system into a smartphone or a smartphone case.

In other embodiments, a handheld object assessment system is disclosed that includes a laser array configured to emit lasers with multiple different wavelengths, a detector array configured to detect reflection of laser emissions at the multiple different wavelengths, and a control system having a memory that stores computer instructions and a processor that executes the computer instructions. The processor-executed computer instructions cause the control system to: initiate laser emissions at the multiple different wavelengths directed towards an object being assessed; detect an amount of the laser emissions at the multiple different wavelengths that were reflected from the object being assessed; determine an amount of laser emissions that were absorbed into the object being assessed at the multiple different wavelengths; determine one or more parameters regarding the object being assessed by comparing the amount of laser emissions that were absorbed and the amount of laser emissions that were reflected; and notify a user of the handheld object assessment system of the one or more parameters of the object being assessed that were determined.

BRIEF DESCRIPTION OF THE DRAWINGS

Non-limiting and non-exhaustive embodiments are described with reference to the following drawings. In the drawings, like reference numerals refer to like parts throughout the various figures unless otherwise specified.

For a better understanding of the present disclosure, reference will be made to the following Detailed Description, which is to be read in association with the accompanying drawings:

FIG. 5 is a component view of an object assessment system that includes a laser array, detector array, and computer for performing chemical analysis of vegetable produce to detect one or more of specific chemicals, pesticides, or allergens, in accordance with embodiments described herein;

DETAILED DESCRIPTION

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

Figure 1:
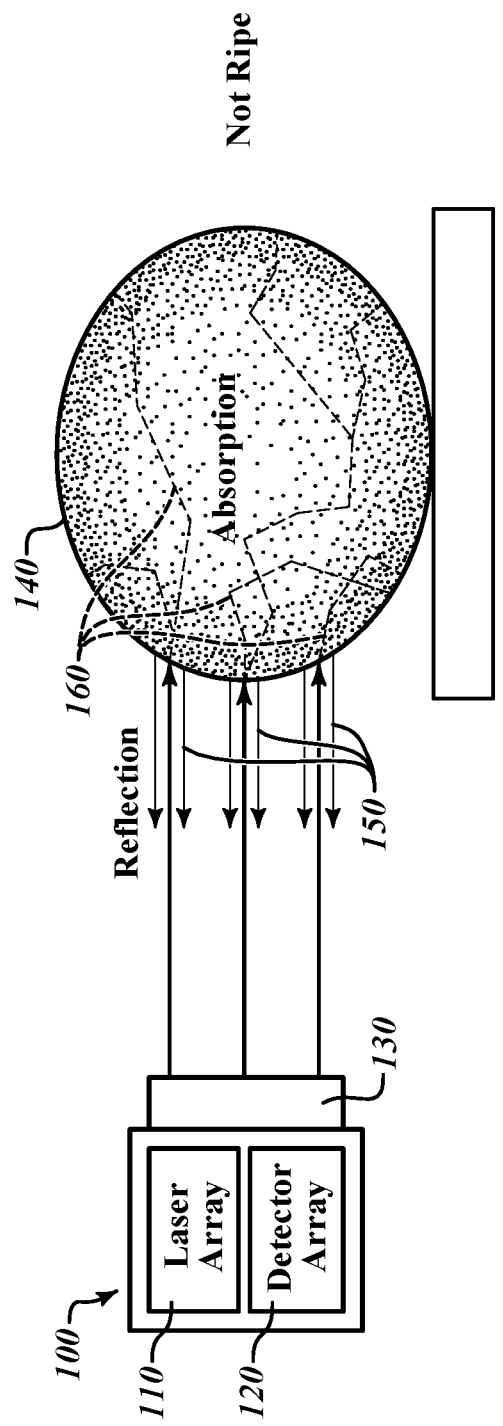
FIG. 1 is a side view of a handheld object assessment system emitting lasers from a laser array at a piece of fruit to discern the ripeness of the fruit and detecting a larger amount of reflection, in accordance with embodiments described herein.
Figure 2:
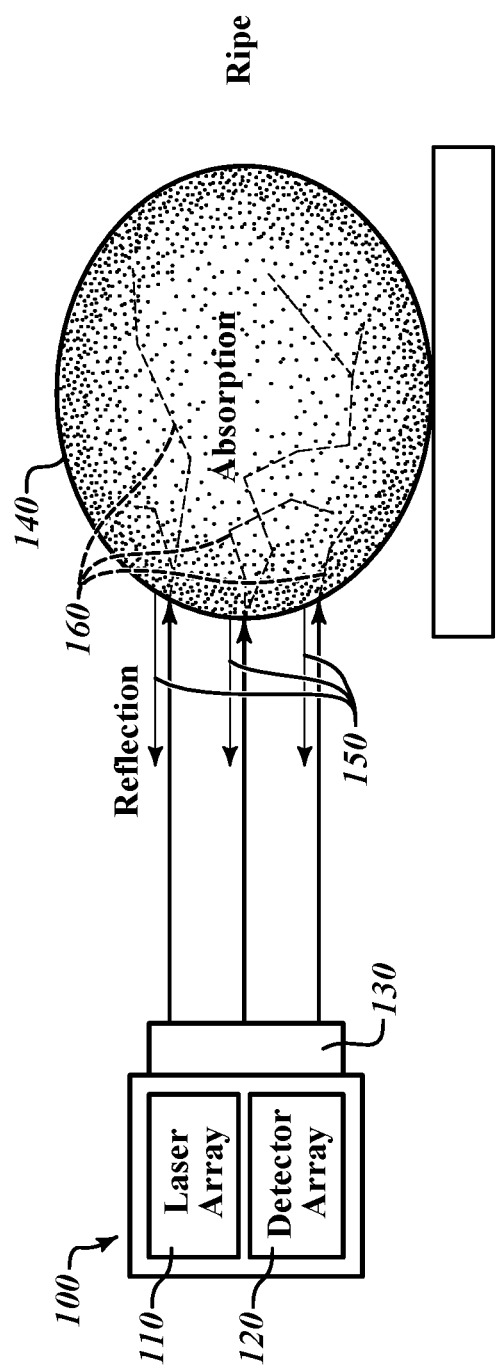
FIG. 2 is a side view of a handheld object assessment system emitting lasers from a laser array at a piece of fruit to discern the ripeness of the fruit and detecting a smaller amount of reflection, in accordance with embodiments described herein.

Referring now to FIGS. 1 and 2, in one or more implementations, a handheld object assessment system 100 is used to analyze objects of interest. The use of optical non-destructive analysis techniques to determine the quality and potential contamination of objects of interest, such as fruits and vegetable, provides efficient and effective analysis. As such, in one or more embodiments, optical non-destructive analysis techniques may be employed to help ensure the selection of safe, appealing, and nutritious food (e.g., fruits and vegetable) by an end user. In some embodiments, optical non-destructive laser techniques are based on analyzing the laser emissions which interact with the object being assessed. The optical non-destructive analysis techniques may then examine the results of the interaction with the laser emissions and the object being assessed. Additionally, or alternatively, the non-destructive analysis techniques may also examine the results of the interaction with the laser emissions in the area just surrounding the object to be assessed, such as "off gassing" from fruits, vegetables, and other non-food objects (e.g., plastics, metals, artificial and nature materials including fibers, as well as anything that produces a smell). Off gassing can naturally occur during the ripening process of fruits and vegetables. Thus, in some embodiments the handheld object assessment system 100 may be used to assess the ripeness of produce, such as by detecting the off gassing levels (i.e., ethylene levels) from the produce.

Additionally, off gassing can artificially occur when organic chemicals are trapped during the manufacture of certain goods. These chemicals eventually are released as particulate matter and gases, sometimes called volatile organic compounds (VOCs). Accordingly, the handheld object assessment system 100 may be used to detect dangerous or otherwise unwanted off gassing from certain manufactured goods.

It is a technological benefit of the handheld object assessment system 100 that the optical laser measurement techniques are non-destructive so the objects that are tested may actually be consumed (e.g., eaten or otherwise used) by an end user, instead of being destroyed in the testing and analysis process. Some laser analysis techniques, such as those that use an excimer laser, actually remove (i.e., vaporize) material from the object that is being assessed. Other techniques require that the object (e.g., fruits, vegetable, or other non-food object) be cut in half, biopsied, or otherwise irreparably damaged. Thus, the analyzed object cannot then be consumed or otherwise used for its intended purpose. Accordingly, the non-destructive nature of the optical non-destructive laser analysis technique employed in the handheld object assessment system 100 is a technological improvement over other destructive analysis systems.

In some embodiments of the handheld object assessment system 100, optical non-destructive laser spectroscopy in the visible and near infrared range is used as an examination method for analyzing chemical and physical properties of biological materials. Spectroscopy may be defined as the measurement and analysis of results produced when emitted electromagnetic radiation interacts with matter. The visible light spectrum is defined as 380-780 nm, and the near infrared spectrum is defined as 780-3000 nm, per ISO 20473. Notably, optical non-destructive laser spectroscopy may be employed in a reflectance mode that distinguishes reflectance (and scattering) from absorption in response to the emitted laser interacting with the object to be assessed (as well as potentially the area immediately adjacent the object to be assessed where off gassing, such as ethylene from fruit, or other chemical disbursements may occur). Optical laser spectroscopy works well when detecting the chemical and physical properties of biological materials such as fruits and vegetable because these biological materials cause absorption at certain wavelengths. This absorption at certain wavelengths may then be contrasted to the reflection and scattering that occur in response to the emitted lasers from the handheld object assessment system 100.

Referring still to FIG. 1, a handheld object assessment system 100 is shown emitting lasers from a laser array 110 at a piece of fruit (i.e., object 140 being assessed) to discern the ripeness of the fruit. In FIG. 1, the detector array 120 of the handheld object assessment system 100 detects a larger amount of reflection 150 (and scattering) than absorption 160 from the object 140 being assessed. The control system 130 of the handheld object assessment system 100 is programed to determine that a ratio of more reflected emissions (and scattered emissions) than absorbed emissions is an indication of ripeness of the fruit.

Referring now to FIG. 2, the handheld object assessment system 100 is again shown emitting lasers from a laser array 110 at the piece of fruit (i.e., object 140 being assessed) to discern the ripeness of the fruit. In FIG. 2, the detector array 120 of the handheld object assessment system 100 detects a smaller amount of reflection 150 (and scattering) than absorption 160 from the object 140 being assessed. The control system 130 of the handheld object assessment system 100 is programmed to determine that a ratio of less reflected emissions (and scattered emissions) than absorbed emissions is an indication of the fruit not being ripe.

Accordingly, when the percentage of absorbed laser emissions is a larger than the percentage of reflected laser emission, the control system 130 determines that this is an indication of ripeness of the fruit or vegetable. Correspondingly, when the percentage of absorbed laser emissions is smaller than the percentage of reflected laser emissions, the control system 130 determines that this is an indication of un-ripeness of the fruit or vegetable. For example, in one embodiment, the handheld object assessment system 100 may emit a 100 milliwatt (mw) laser, and 75 mw are absorbed by the object 140 (e.g., fruit or vegetable), while 25 mw are reflected (or otherwise scattered) from the object 140. Since this would represent a percentage of absorbed laser emissions that is larger than the percentage of reflected laser emissions, the control system 130 determines that this is an indication of ripeness of the fruit or vegetable.

Furthermore, not only may there be absorption 160 at certain wavelengths from the object 140 to be assessed itself, there may also be absorption 160 at certain wavelengths from additives or contaminants of the object 140. Many other chemical materials, biological materials, and allergens also cause absorption 160 at certain wavelengths. Thus, the optical laser spectroscopy of the handheld object assessment system 100 also works well for detecting the chemical and physical properties of materials other than fruits and vegetable. For example, in some embodiments the handheld object assessment system 100 is not just used to assess the ripeness of produce, but may also be used to determine what, if any, pesticides were used (either intentionally or unintentionally) on the produce.

Figure 3:
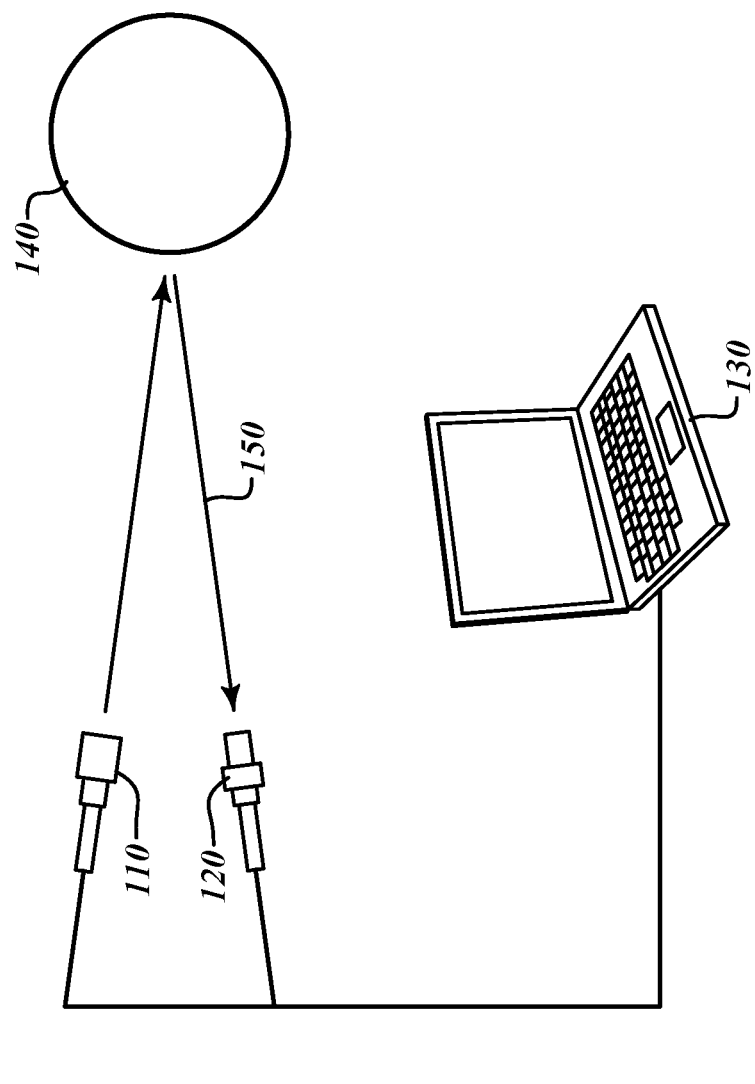
FIG. 3 is a component view of an object assessment system that has physically separated but operatively connected components that include a laser array, detector array, and remote server for assessing one or more parameters of an object, in accordance with embodiments described herein.

Referring now to FIG. 3, a component view is shown of a handheld object assessment system 100 that includes a laser array 110, detector array 120, and computer 150 (that includes the control system 130) for performing chemical analysis of an object 140 to be assessed (e.g., vegetable produce) to detect one or more of specific chemicals, pesticides, or allergens. Notably, the embodiment of FIG. 3 shows that the laser array 110, detector array 120, and the control system 130 do not have to be housed in the same device. While in FIGS. 1 and 2, the laser array 110, detector array 120, and the control system 130 all are housed in the same device, FIG. 3 shows an embodiment with more spatially distributed components.

In another implementation, the handheld object assessment system 100 may not just be used to assess the ripeness of produce, but may also be used to determine what chemicals may have contaminated the produce. In still another implementation, the handheld object assessment system and method may not just be used to assess the ripeness of produce, but may also be used to determine what biological agents (e.g., bacteria, insects, etc.) may have contaminated the produce. In yet another implementation, the handheld object assessment system and method may not just be used to assess the ripeness of produce, but may also be used to determine what allergens (e.g., peanut, milk, egg, fish, shellfish, tree nuts, wheat, soy, and the like) may have been associated with the produce. Therefore, since there is absorption at certain wavelengths from additives, allergens, or contaminates of the object, some embodiments of the handheld object assessment system 100 are tuned to appropriate wavelengths to identify these additives, allergens, or contaminates.

In still other embodiments of the handheld object assessment system 100, assessment may be performed on other non-food objects or locations, such as physical objects, outdoor environments, residential locations, workplace locations, animals, people, consumer products, areas with air-quality concerns (e.g., $CO_2$ contamination), and the like.

Figure 7:
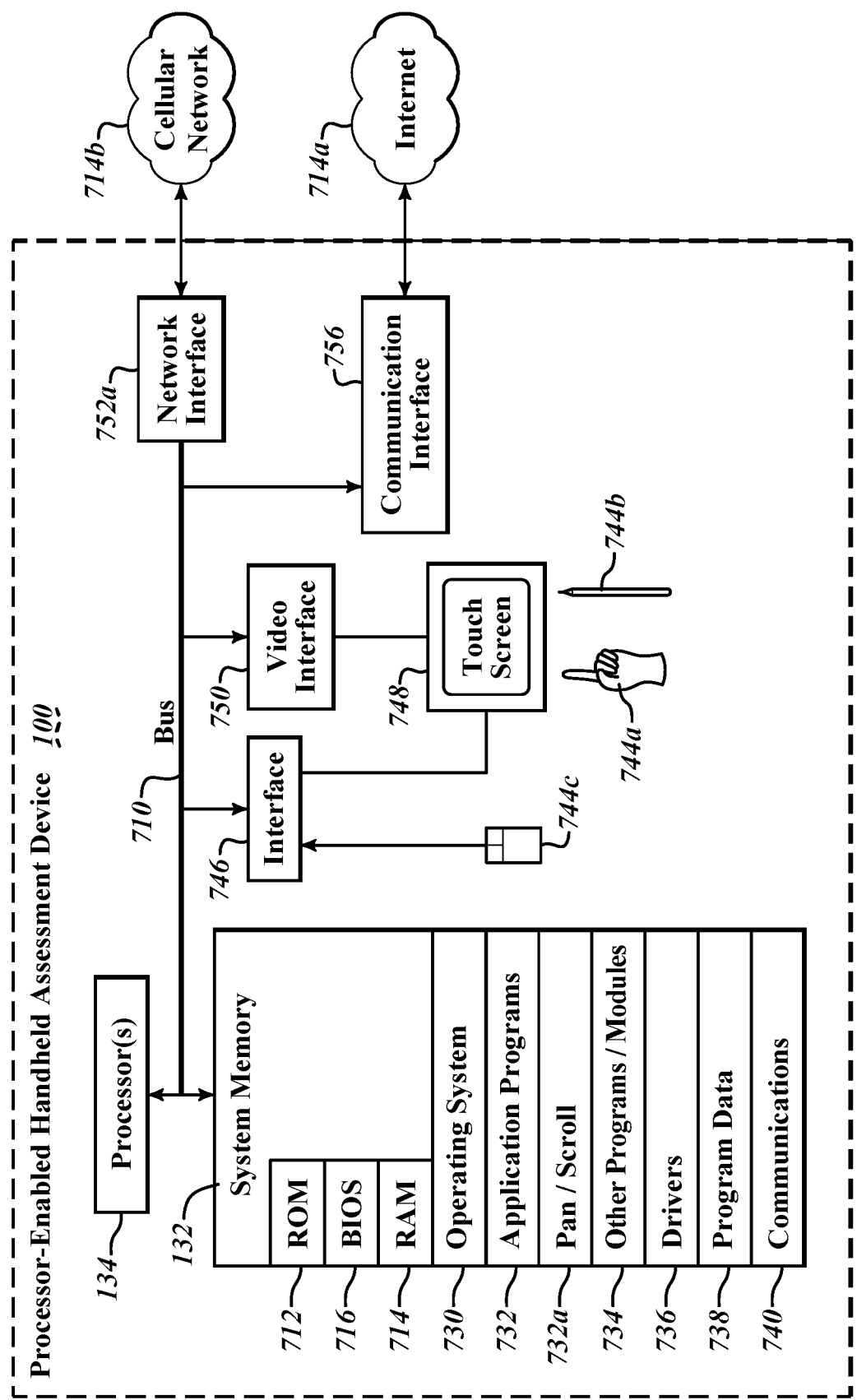
FIG. 7 is a block diagram of an example processor based device used to implement the handheld object assessment system, as described herein.

In some embodiments of the handheld object assessment system 100, the assessment system includes a laser array 110 configured to emit lasers with multiple different wavelengths, a detector array 120 configured to detect reflection 150 of laser emissions at the multiple different wavelengths, and a control system 130 having a system memory 132 that stores computer instructions and a processor 134 that executes the computer instructions, as shown in FIG. 7. In one or more implementations, the lasers used by the laser array 110 are diode lasers. In other implementations, other appropriate lasers with low power consumption may be employed.

Referring again to FIGS. 1 and 2, in some aspects of the handheld object assessment system 100, the control system 130 initiates laser emissions from the laser array 110 at the multiple different wavelengths that are directed towards an object 140 to be assessed. In one or more embodiments, laser emissions are emitted from the laser array 110 at least at three different wavelengths to assist with normalizing and validating the results of the visible and near infrared optical laser spectroscopy (e.g., one or more lasers are emitted at wavelengths in the visible spectrum and one or more lasers are emitted in at wavelengths in the near infrared spectrum). In one non-limiting embodiment, the three distinct wavelengths are 850 nanometers, 1380 nanometers, and 1850 nanometers. In another non-limiting embodiment, the handheld object assessment system 100 initiates laser emissions from the laser array 110 at three distinct wavelength ranges that include 750-950 nanometers, 1280-1480 nanometers, and 1750-1950 nanometers. In some embodiments of the handheld object assessment system 100, the laser array 110 of the handheld object assessment system 100 includes a plurality of lasers configured to emit laser emissions that are fixed at specific wavelengths. In other embodiments of the handheld object assessment system 100, the laser array 110 of the handheld object assessment system 100 emits laser emissions that are tunable within a range of specific wavelengths.

In another aspect of the handheld object assessment system 100, the detector array 120 detects an amount of the laser emissions that were reflected from the object 140 being assessed. As described above, the detector array 120 detects an amount of the laser emissions that were reflected from the object 140 at the multiple different wavelengths. These reflections 150 may be direct reflections and may also include scattered reflections. Using the detected reflections 150 of the laser emissions from the object 140 being assessed and the initiated laser emissions directed towards the object 140 being assessed, the control system 130 determines an amount of laser emissions that were absorbed into the object being assessed. In another aspect of some embodiments, other spectroscopy detection techniques are used to determine the amount of laser emissions that were absorbed into the object 140 being assessed.

In still another aspect of the handheld object assessment system 100, the control system 130 determines one or more parameters of the object 140 being assessed by comparing the amount of laser emissions that were absorbed into the object 140 being assessed and the amount of laser emissions that were reflected from the object 140 being assessed. The one or more parameters of the object 140 being assessed may include one or more of the ripeness of a fruit or vegetable, un-ripeness of a fruit or vegetable, rottenness of a fruit or vegetable, pesticide presence on a fruit or vegetable, allergen presence on a fruit or vegetable (e.g., peanuts, animal dander, etc.), chemical contamination of a fruit or vegetable, insect contamination of a fruit or vegetable, off gassing of a non-food article or device, presence of a gas (e.g., $CO_2$, etc.) in a room or outdoor location, presence of a chemical in a room or outdoor location, and presence of a biological agent in a room or outdoor location.

Figure 4A:
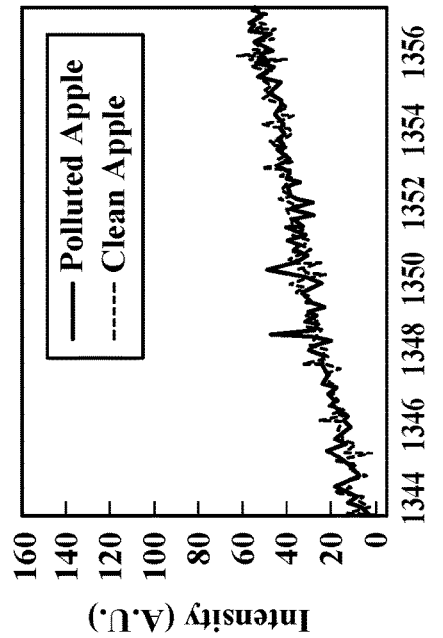
FIGS. 4A, 4B, and 4C are chemical analysis charts at different wavelength ranges that show identified parameters of the assessed object in accordance with embodiments described herein.
Figure 4B:
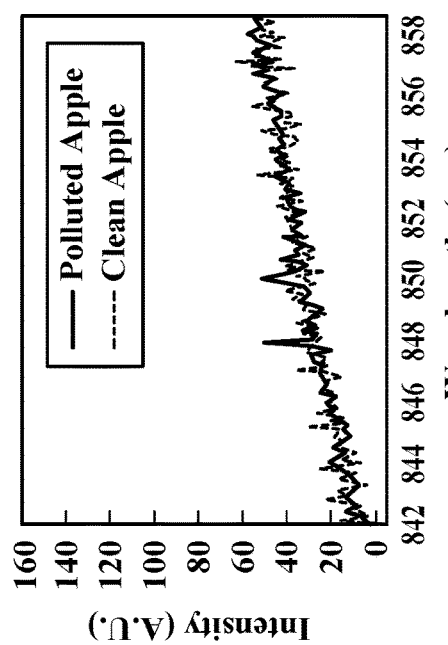
Figure 4C:
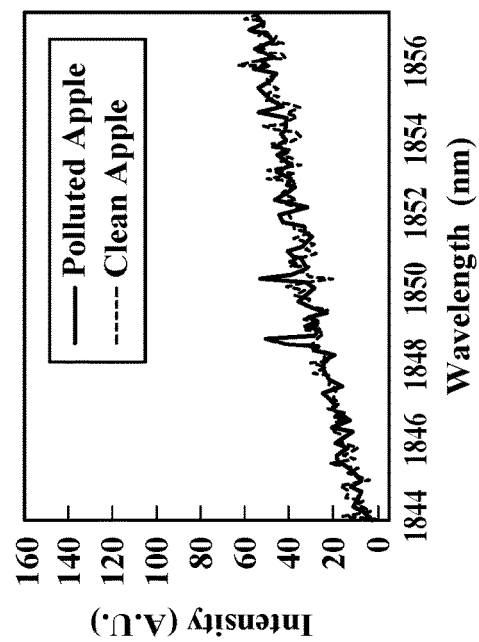

In yet another aspect, the handheld object assessment system 100 notifies a user of the handheld object assessment system of the one or more determined parameters of the object 140 being assessed. As shown in FIGS. 4A, 4B, and 4C, in some embodiments the handheld object assessment system 100 notifies a user of the one or more determined parameters of the object 140 being assessed using chemical analysis charts at different wavelength ranges that show identified parameters of the assessed object.

Referring again to FIGS. 1 and 2, in various embodiments of the handheld object assessment system 100, this notification is made in different manners. In some embodiments, the handheld object assessment system 100 includes a display screen on which the notification is made to the user of the one or more determined parameters of the object 140 being assessed. In other embodiments, the handheld object assessment system 100 includes a speaker that is configured to audibly announce the notification to the user of the one or more determined parameters of the object 140 being assessed. In still other embodiments, the handheld object assessment system 100 includes a communication system that is configured to transmit the notification to another component of the user (e.g., smartwatch, smartphone, computer, etc.) of the one or more determined parameters of the object 140 being assessed. In yet other embodiments, the handheld object assessment system 100 includes a haptic system that is configured to vibrate a notification to the user of the one or more determined parameters of the object 140 being assessed. In another aspect, a user can select options with respect to the type of object being assessed, parameters associated with the laser array 110, parameters associated with the detector array 120, distance from the object, type of analysis to be performed, method of notifying the user of the results of the analysis, and the like.

In some implementations, the handheld object assessment system 100 is incorporated directly into a smartphone and uses the native laser components and detector components of the smartphone. In other implementations, the handheld object assessment system 100 is integrated into a smartphone case that mounts onto the smartphone itself. In still other implementations, the handheld object assessment system 100 is a separate device with no physical connection to a smartphone. These non-integrated implementations provide the option to select the lasers for the laser array 110 and the detectors for the detector array 120 without requiring coordination from the smartphone manufacturer.

In implementations where the handheld object assessment system 100 is separate from the smartphone (i.e., not integrated into the smartphone), the handheld object assessment system 100 may communicate with an application that is installed on the smartphone. In some embodiments, the handheld object assessment system 100 communicates with an application that is installed on the smartphone via a 5G network. A 5G network provides a broad range of wireless services delivered to the end user across multiple access platforms and multi-layer networks. 5G is a dynamic, coherent and flexible framework of multiple advanced technologies supporting a variety of applications. 5G utilizes an intelligent architecture, with Radio Access Networks (RANs) not constrained by base station proximity or complex infrastructure. 5G enables a disaggregated, flexible, and virtual RAN with interfaces creating additional data access points.

Referring now to FIG. 5, a handheld object assessment system 100 is shown that includes a laser array 110, a detector array 120, a control system 130, and a computer 170. The handheld object assessment system 100 performs chemical analysis of vegetable produce to detect one or more of specific chemicals, pesticides, or allergens. In many embodiments, all of the calculations performed by the handheld object assessment system 100 during the analysis operations are performed locally by the control system 130 of the handheld object assessment system 100. In other embodiments, some of the calculations that are performed during the analysis operations are performed locally by the control system 130, and some are performed on a local smartphone (not shown) running a software application in communication with the handheld object assessment system 100. In still other embodiments, some of the calculations that are performed during the analysis operations are performed locally by the control system 130, some of the calculations are performed on a local smartphone (not shown) running a software application in communication with the handheld object assessment system 100, and some of the calculations are performed by a computer 170 in communication with the handheld object assessment system 100. In yet other embodiments, none of the calculations are performed on the computer 170, but the computer 170 is used to store information (e.g., laser data, detector data, object data, analysis data, etc.) for the handheld object assessment system 100.

Referring now to another aspect of the handheld object assessment system 100, in some embodiments a machine learning engine is trained to assist with the analyses performed by the handheld object assessment system 100. Otherwise stated, instead of having the control system 130 of the handheld object assessment system 100 simply use fixed equations to determine parameters of objects 140 being assessed (e.g., ripeness of fruit, ripeness of vegetable, presence of pesticides, presence of soy, presence of wheat, presence of dairy, presence of specific chemical, presence of specific insect, presence of specific biological agent, etc.), the control system 130 of the handheld object assessment system 100 includes or works in conjunction with a machine learning engine that is trained with training data on how to interpret the parameters of objects 140 being assessed (e.g., ripeness of fruit, ripeness of vegetable, presence of pesticides, presence of soy, presence of wheat, presence of dairy, presence of specific chemical, presence of specific insect, presence of specific biological agent, etc.).

In some embodiments, each handheld object assessment system 100 is associated with a single machine learning engine that is trained for a specific object and specific parameter assessment (e.g., peach and ripeness, spinach and pesticides, cookies and peanut allergen, or pillow and cat dander, etc.). In other embodiments, each handheld object assessment system 100 is associated with a multiple machine learning engines, each of which is trained for a specific object and specific parameter assessment (e.g., peach and ripeness, spinach and pesticides, cookies and peanut allergen, or pillow and cat dander, etc.). In such embodiments, where the handheld object assessment system 100 is associated with multiple machine learning engines, the multiple machine learning engines associated with handheld object assessment system 100 may be located in one or more remote computers or servers due to the processing and data storage capacity requirements associated with multiple machine learning engines.

Furthermore, in another aspect of some handheld object assessment systems 100, each handheld object assessment system 100 is configured to receive user input regarding the success or failure of the determination of one or more parameters of the object being assessed. In some such embodiments, the handheld object assessment system 100 includes a user input device, such as a touchscreen 160 for the user to enter input regarding the success or failure of the parameter determination. In other such embodiments, the user employs a software application on a smartphone associated with the handheld object assessment system 100 to enter input regarding the success or failure of the parameter determination.

This input from the user regarding the success or failure of the parameter determination may be used to further train the machine learning engine and even personalize the handheld object assessment system 100. For example, in one embodiment the handheld object assessment system 100 may have a machine learning engine that is trained to determine if a peach is ripe. The user may employ the handheld object assessment system 100 to determine if a peach is ripe, and receive results that the peach is ripe. In this embodiment, the user may personally feel that the peach is not as ripe as they would like it to be, so the user may enter user input into the handheld object assessment system 100 (and the associated machine learning engine) that the previous laser reflection/absorption results should be categorized as "not ripe" instead of "ripe," and stronger results are needed to achieve the results category of ripe for a peach for this user. This may be considered further supervised training of the peach ripeness machine learning engine.

In another embodiment, the handheld object assessment system 100 may have a machine learning engine that is trained to determine if a cookie is contaminated with peanut allergens. The user may employ the handheld object assessment system 100 to determine if a cookie contains peanut allergens, and receive results that the cookie does not contain peanut allergens (but actually while the peanut allergen level is "acceptably" low according to previous training levels, the level is not zero). In this embodiment, the user may personally feel that the peanut allergen level is still too high since the user has a particularly strong peanut allergy. Thus, the user may enter user input into the handheld object assessment system 100 (and the associated machine learning engine) that the previous laser reflection/absorption results should be categorized as "peanut allergen level too high" instead of "peanut allergen level acceptable," and even lower levels are needed to achieve the results category of "peanut allergen level acceptable" for this user. This may be considered further supervised training of the peanut allergen machine learning engine.

In still another embodiment, the handheld object assessment system 100 may have a machine learning engine that is trained to determine if cat dander is present on a pillow or beddings. The user may employ the handheld object assessment system 100 to determine if a pillow or beddings are free from cat dander, and receive results that the pillow or beddings are cat dander-free (but actually while the cat dander level is "acceptably" low according to previous training levels, the level is not zero). In this embodiment, the user may personally feel that the cat dander level is still too high since the user has a particularly strong cat allergy. Thus, the user may enter user input into the handheld object assessment system 100 (and the associated machine learning engine) that the previous laser reflection/absorption results should be categorized as "cat allergen level too high" instead of "cat allergen level acceptable," and even lower levels are needed to achieve the results category of "cat allergen level acceptable" for this user. This may be considered further supervised training of the cat allergen machine learning engine.

In yet another embodiment, the handheld object assessment system 100 may have a machine learning engine that is trained to determine if pesticides are present on spinach. The user may employ the handheld object assessment system 100 to determine if spinach is free from pesticides, and receive results that the spinach is free from pesticides (but actually while the pesticide level is "acceptably" low according to previous training levels, the level is not zero). In this embodiment, the user may personally feel that the pesticide level is still too high since the user has a particularly strong sensitivity to pesticides. Thus, the user may enter user input into the handheld object assessment system 100 (and the associated machine learning engine) that the previous laser reflection/absorption results should be categorized as "pesticide level too high" instead of "pesticide level acceptable," and even lower levels are needed to achieve the results category of "pesticide level acceptable" for this user. This may be considered further supervised training of the pesticide machine learning engine.

Although embodiments described herein are referred to as using one or more machine learning engines or artificial neural networks to identify parameters of objects, embodiments are not so limited and other computer vision algorithms or techniques may be used. For example, in some embodiments, shape-based algorithms, color-based algorithms, or other visual machine learning techniques may be employed to identify objects. In some embodiments, the computer vision algorithms or techniques may be selected by a user based on the type of object (e.g., fruit, vegetable, other food item, non-food item, article of manufacture, indoor space, outdoor space, etc.) being identified or the conditions of the target geographical area. In yet other embodiments, machine learning techniques may be employed to learn which computer vision algorithms or techniques are most accurate or efficient for a type of object or condition.

Figure 6:
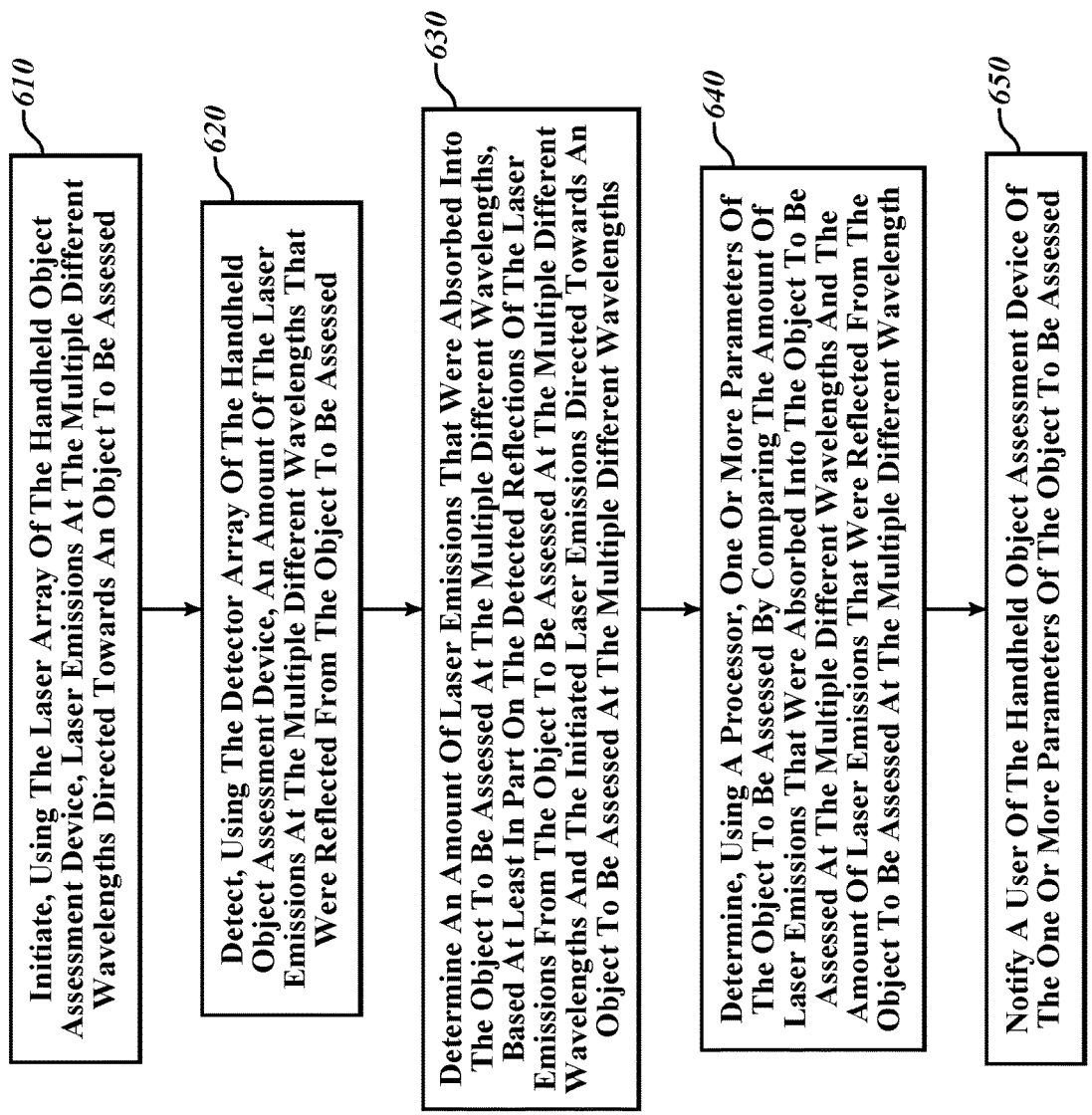
FIG. 6 is a logic diagram of a method of analyzing an object being assessed using the handheld object assessment system in accordance with embodiments described herein.

FIG. 6 is a logic diagram showing a handheld object assessment method. As shown in FIG. 6, at operation 610, the method includes initiating, using the laser array 110, laser emissions at the multiple different wavelengths directed towards an object to be assessed in response to the laser emissions reaching the object 140 to be assessed. At operation 620, the method includes detecting, using the detector array 120, an amount of the laser emissions at the multiple different wavelengths that were reflected from the object 140 to be assessed. At operation 630, the method includes determining, from the detected reflections 150 of the laser emissions from the object 140 to be assessed at the multiple different wavelengths and the initiated laser emissions at the multiple different wavelengths directed towards an object to be assessed, an amount of laser emissions that were absorbed into the object to be assessed at the multiple different wavelengths. At operation 640, the method includes determining, using a processor 134, one or more parameters of the object 140 to be assessed by comparing the amount of laser emissions that were absorbed into the object to be assessed at the multiple different wavelengths and the amount of laser emissions that were reflected from the object to be assessed at the multiple different wavelengths. At operation 650, the method includes notifying a user of the handheld object assessment system of the one or more parameters of the object 140 to be assessed.

For use in conjunction with the handheld object assessment system and method, FIG. 7 shows a processor-based device suitable for implementing the handheld object assessment system and method. Although not required, some portion of the implementations will be described in the general context of processor-executable instructions or logic, such as program application modules, objects, or macros being executed by one or more processors. Those skilled in the relevant art will appreciate that the described implementations, as well as other implementations, can be practiced with various processor-based system configurations, including handheld devices, such as smartphones and tablet computers, wearable devices, multiprocessor systems, microprocessor-based or programmable consumer electronics, personal computers (PCs), network PCs, minicomputers, mainframe computers, and the like.

In the system for stereo camera vision system, the processor-based device may include one or more processors 134, a system memory 132 and a system bus 710 that couples various system components including the system memory 132 to the processor(s) 134. The processor-based device will, at times, be referred to in the singular herein, but this is not intended to limit the implementations to a single system, since in certain implementations, there will be more than one system or other networked computing device involved. Non-limiting examples of commercially available systems include, but are not limited to, ARM processors from a variety of manufactures, Core microprocessors from Intel Corporation, U.S.A., PowerPC microprocessor from IBM, Sparc microprocessors from Sun Microsystems, Inc., PA-RISC series microprocessors from Hewlett-Packard Company, and 68xxx series microprocessors from Motorola Corporation. The system memory 132 may be located on premises or it may be cloud based.

The processor(s) 134 in the processor-based devices of the system for stereo camera vision system may be any logic processing unit, such as one or more central processing units (CPUs), microprocessors, digital signal processors (DSPs), application-specific integrated circuits (ASICs), field programmable gate arrays (FPGAs), and the like. Unless described otherwise, the construction and operation of the various blocks shown in FIG. 7 are of conventional design. As a result, such blocks need not be described in further detail herein, as they will be understood by those skilled in the relevant art.

The system bus 710 in the processor-based devices of the system for stereo camera vision system can employ any known bus structures or architectures, including a memory bus with a memory controller, a peripheral bus, and a local bus. The system memory 132 includes read-only memory (ROM) 712 and random access memory (RAM) 714. A basic input/output system (BIOS) 716, which can form part of the ROM 712, contains basic routines that help transfer information between elements within the processor-based device, such as during start-up. Some implementations may employ separate buses for data, instructions and power.

The processor-based device of the system for stereo camera vision system may also include one or more solid state memories; for instance, a Flash memory or solid state drive (SSD), which provides nonvolatile storage of computer-readable instructions, data structures, program modules and other data for the processor-based device. Although not depicted, the processor-based device can employ other nontransitory computer- or processor-readable media, for example, a hard disk drive, an optical disk drive, or a memory card media drive.

Program modules in the processor-based devices of the system for stereo camera vision system can be stored in the system memory 132, such as an operating system 730, one or more application programs 732, other programs or modules 734, drivers 736 and program data 738.

The application programs 732 may, for example, include panning/scrolling logic 732a. Such panning/scrolling logic may include, but is not limited to, logic that determines when and/or where a pointer (e.g., finger, stylus, cursor) enters a user interface element that includes a region having a central portion and at least one margin. Such panning/scrolling logic may include, but is not limited to, logic that determines a direction and a rate at which at least one element of the user interface element should appear to move, and causes updating of a display to cause the at least one element to appear to move in the determined direction at the determined rate. The panning/scrolling logic 732a may, for example, be stored as one or more executable instructions. The panning/scrolling logic 732a may include processor and/or machine executable logic or instructions to generate user interface objects using data that characterizes movement of a pointer, for example, data from a touch-sensitive display or from a computer mouse or trackball, or other user interface device.

The system memory 132 in the processor-based devices of the system for stereo camera vision system may also include communications programs 740, for example, a server and/or a Web client or browser for permitting the processor-based device to access and exchange data with other systems such as user computing systems, websites on the Internet, corporate intranets, or other networks as described below. The communications program 740 in the depicted implementation is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

While shown in FIG. 7 as being stored in the system memory 132, operating system 730, application programs 732, other programs/modules 734, drivers 736, program data 738 and server and/or browser can be stored on any other of a large variety of nontransitory processor-readable media (e.g., hard disk drive, optical disk drive, SSD and/or flash memory).

A user of a processor-based device in the system for stereo camera vision system can enter commands and information via a pointer, for example, through input devices such as a touch screen 748 via a finger 744a, stylus 744b, or via a computer mouse or trackball 744c which controls a cursor. Other input devices can include a microphone, joystick, game pad, tablet, scanner, biometric scanning device, and the like. These and other input devices (i.e., I/O devices) are connected to the processor(s) 134 through an interface 746 such as a touch-screen controller and/or a universal serial bus (USB) interface that couples user input to the system bus 710, although other interfaces such as a parallel port, a game port or a wireless interface or a serial port may be used. The touch screen 748 can be coupled to the system bus 710 via a video interface 750, such as a video adapter to receive image data or image information for display via the touch screen 748. Although not shown, the processor-based device can include other output devices, such as speakers, vibrator, haptic actuator or haptic engine, and the like.

The processor-based devices of the system for stereo camera vision system operate in a networked environment using one or more of the logical connections to communicate with one or more remote computers, servers and/or devices via one or more communications channels, for example, one or more networks 714a, 714b. These logical connections may facilitate any known method of permitting computers to communicate, such as through one or more LANs and/or WANs, such as the Internet, and/or cellular communication networks. Such networking environments are well known in wired and wireless enterprise-wide computer networks, intranets, extranets, the Internet, and other types of communication networks including telecommunication networks, cellular networks, paging networks, and other mobile networks.

When used in a networking environment, the processor-based devices of the system for stereo camera vision system may include one or more network, wired or wireless communications interfaces 752a, 756 (e.g., network interface controllers, cellular radios, Wi-Fi radios, Bluetooth radios) for establishing communications over the network, for instance, the Internet 714a or cellular network 714b.

In a networked environment, program modules, application programs, or data, or portions thereof, can be stored in a server computing system (not shown). Those skilled in the relevant art will recognize that the network connections shown in FIG. 7 are only some examples of ways of establishing communications between computers, and other connections may be used, including wirelessly.

For convenience, the processor(s) 134, system memory 132, and network and communications interfaces 752a, 756 are illustrated as communicably coupled to each other via the system bus 710, thereby providing connectivity between the above-described components. In alternative implementations of the processor-based device, the above-described components may be communicably coupled in a different manner than illustrated in FIG. 7. For example, one or more of the above-described components may be directly coupled to other components, or may be coupled to each other, via intermediary components (not shown). In some implementations, system bus 710 is omitted, and the components are coupled directly to each other using suitable connections.

Throughout this specification and the appended claims the term "communicative" as in "communicative pathway," "communicative coupling," and in variants such as "communicatively coupled," is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), one or more communicative link(s) through one or more wireless communication protocol(s), and/or optical pathways (e.g., optical fiber), and exemplary communicative couplings include, but are not limited to, electrical couplings, magnetic couplings, wireless couplings, and/or optical couplings.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," "to, at least, provide," "to, at least, transmit," and so on.

The above description of illustrated implementations, including what is described in the Abstract, is not intended to be exhaustive or to limit the implementations to the precise forms disclosed. Although specific implementations of and examples are described herein for illustrative purposes, various equivalent modifications can be made without departing from the spirit and scope of the disclosure, as will be recognized by those skilled in the relevant art. The teachings provided herein of the various implementations can be applied to other portable and/or wearable electronic devices, not necessarily the exemplary wearable electronic devices generally described above.

For instance, the foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs executed by one or more computers (e.g., as one or more programs running on one or more computer systems), as one or more programs executed by one or more controllers (e.g., microcontrollers) as one or more programs executed by one or more processors (e.g., microprocessors, central processing units, graphical processing units), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any processor-readable medium for use by or in connection with any processor-related system or method. In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

Operations of processes described herein can be performed in any suitable order unless otherwise indicated herein or otherwise clearly contradicted by context. The processes described herein (or variations and/or combinations thereof) are performed under the control of one or more computer systems configured with executable instructions and are implemented as code (e.g., executable instructions, one or more computer programs or one or more applications) executing collectively on one or more processors, by hardware or combinations thereof. In an embodiment, the code is stored on a computer-readable storage medium, for example, in the form of a computer program comprising a plurality of instructions executable by one or more processors. In an embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In an embodiment, code (e.g., executable code or source code) is stored on a set of one or more non-transitory computer-readable storage media having stored thereon executable instructions that, when executed (i.e., as a result of being executed) by one or more processors of a computer system, cause the computer system to perform operations described herein. The set of non-transitory computer-readable storage media, in an embodiment, comprises multiple non-transitory computer-readable storage media, and one or more of individual non-transitory storage media of the multiple non-transitory computer-readable storage media lacks all of the code while the multiple non-transitory computer-readable storage media collectively store all of the code. In an embodiment, the executable instructions are executed such that different instructions are executed by different processors—for example, a non-transitory computer-readable storage medium stores instructions and a main CPU executes some of the instructions while a graphics processor unit executes other instructions. In an embodiment, different components of a computer system have separate processors, and different processors execute different subsets of the instructions.

Accordingly, in an embodiment, computer systems are configured to implement one or more services that singly or collectively perform operations of processes described herein, and such computer systems are configured with applicable hardware and/or software that enable the performance of the operations.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure. All references, including publications, patent applications, and patents, cited herein are hereby incorporated by reference to the same extent as if each reference were individually and specifically indicated to be incorporated by reference and were set forth in its entirety herein.

The invention claimed is:

1. A system for assessing an object, comprising: a handheld object assessment system that includes a laser array configured to emit lasers, a detector array configured to detect reflections of laser emissions, and a control system having a memory that stores computer instructions and a processor that when executing the computer instructions causes the control system to: initiate, using the laser array, laser emissions at multiple different wavelengths directed towards an object being assessed; detect, using the detector array, an amount of the laser emissions at the multiple different wavelengths that were reflected from the object being assessed; determine, using the processor, an amount of laser emissions that were absorbed into the object being assessed at the multiple different wavelengths, based at least in part on the detected reflections of the laser emissions from the object being assessed and the initiated laser emissions directed towards an object being assessed; determine, using the processor, one or more parameters of the object being assessed by comparing the amount of laser emissions that were absorbed into the object being assessed at the multiple different wavelengths and the amount of laser emissions that were reflected from the object being assessed at the multiple different wavelengths; and notify a user of the handheld object assessment system of the one or more parameters of the object being assessed that were determined;

wherein the object being assessed potentially includes one or more of a detectable chemical agent, biological agent, and allergen, wherein the first parameter of the one or more parameters of the object being assessed is a presence of the one or more of the chemical agent, biological agent, and allergen, and wherein the second parameter of the one or more parameters of the object being assessed is an absence of the one or more of the chemical agent, biological agent, or allergen.

2. The system of claim 1, wherein the laser array of the handheld object assessment system is configured to emit lasers at three distinct wavelengths towards the object being assessed.

3. The system of claim 2, wherein the three distinct wavelengths are 850 nanometers, 1380 nanometers, and 1850 nanometers.

4. The system of claim 1, wherein the three distinct wavelengths are in a range of 750-950 nanometers, 1280-1480 nanometers, and 1750-1950 nanometers.

5. The system of claim 1, wherein a larger percentage of absorbed laser emissions with respect to reflected laser emissions indicates a first parameter of the one or more parameters of the object being assessed, and a smaller percentage of absorbed laser emissions with respect to reflected laser emissions indicates a second parameter of the one or more parameters of the object being assessed.

6. The system of claim 1, wherein the object being assessed is a fruit or vegetable, and the first parameter of the one or more parameters is a first state of ripeness and the second parameter of the one or more parameters is a second state of ripeness.

7. The system of claim 1, wherein the object being assessed potentially includes one or more of a chemical agent, biological agent, and allergen, wherein the first parameter of the one or more parameters of the object being assessed is a presence of the one or more of the chemical agent, biological agent, and allergen, and wherein the second parameter of the one or more parameters of the object being assessed is an absence of the one or more of the chemical agent, biological agent, and allergen.

8. The system of claim 1, wherein the laser array of the handheld object assessment system includes a plurality of lasers configured to emit laser emissions that are fixed at specific wavelengths.

9. The system of claim 1, wherein the laser array of the handheld object assessment system emits laser emissions that are tunable within specific wavelength ranges.

10. The system of claim 1, further comprising: a remote server in communication with the handheld object assessment system, wherein the remote server performs a chemical analysis of the object being assessed to determine one or more parameters regarding the object being assessed.

11. A method of assessing an object, comprising: initiating, using a laser array, laser emissions at multiple different wavelengths directed towards an object being assessed; detecting, using a detector array, an amount of the laser emissions at the multiple different wavelengths that were reflected from the object being assessed; determining, from the detected reflections of the laser emissions from the object being assessed at the multiple different wavelengths and the initiated laser emissions at the multiple different wavelengths directed towards an object being assessed, an amount of laser emissions that were absorbed into the object being assessed at the multiple different wavelengths; determining, using a processor, one or more parameters of the object being assessed by comparing the amount of laser emissions that were absorbed into the object being assessed at the multiple different wavelengths and the amount of laser emissions that were reflected from the object being assessed at the multiple different wavelengths; and notifying a user of the handheld object assessment system of the one or more parameters of the object being assessed that were determined;

wherein the object being assessed potentially includes one or more of a detectable chemical agent, biological agent, and allergen, wherein the first parameter of the one or more parameters of the object being assessed is a presence of the one or more of the chemical agent, biological agent, and allergen, and wherein the second parameter of the one or more parameters of the object being assessed is an absence of the one or more of the chemical agent, biological agent, or allergen.

12. The method of claim 11, further comprising: emitting lasers from the laser array at three distinct wavelengths towards the object being assessed.

13. The method of claim 12, wherein the three distinct wavelengths of lasers emitted from the laser array are 850 nanometers, 1380 nanometers, and 1850 nanometers.

14. The method of claim 12, wherein the three distinct wavelengths of lasers emitted from the laser array are in a range of 750-950 nanometers, 1280-1480 nanometers, and 1750-1950 nanometers.

15. The method of claim 11, wherein a larger percentage of absorbed laser emissions with respect to the reflected laser emissions indicates a first parameter of the one or more parameters of the object being assessed, and a smaller percentage of absorbed laser emissions with respect to the reflected laser emissions indicates a second parameter of the one or more parameters of the object being assessed.

16. The method of claim 11, wherein the object being assessed is a fruit or vegetable, and the first parameter of the one or more parameters is a first state of ripeness and the second parameter of the one or more parameters is a second state of ripeness.

17. The method of claim 11, further comprising: constructing the laser array of the handheld object assessment system to include a plurality of lasers configured to emit laser emissions that are fixed at specific wavelengths.

18. The method of claim 11, further comprising: constructing the laser array of the handheld object assessment system to produce laser emissions that are tunable with specific wavelength ranges.

19. A handheld object assessment system, comprising: a laser array configured to emit lasers with multiple different wavelengths; a detector array configured to detect reflection of laser emissions at the multiple different wavelengths; and a control system having a memory that stores computer instructions and a processor that when executing the computer instructions causes the control system to: initiate laser emissions at the multiple different wavelengths directed towards an object being assessed; detect an amount of the laser emissions at the multiple different wavelengths that were reflected from the object being assessed; determine an amount of laser emissions that were absorbed into the object being assessed at the multiple different wavelengths; perform a chemical analysis and determine one or more parameters regarding the object being assessed by comparing the amount of laser emissions that were absorbed and the amount of laser emissions that were reflected; and notify a user of the handheld object assessment system of the one or more parameters of the object being assessed that were determined;

wherein the object being assessed potentially includes one or more of a detectable chemical agent, biological agent, and allergen, wherein the first parameter of the one or more parameters of the object being assessed is a presence of the one or more of the chemical agent, biological agent, and allergen, and wherein the second parameter of the one or more parameters of the object being assessed is an absence of the one or more of the chemical agent, biological agent, or allergen.

* * * * *